(12) United States Patent
Belman

(10) Patent No.: US 11,253,282 B2
(45) Date of Patent: Feb. 22, 2022

(54) DISSECTION AND LIGATION CARTRIDGE

(71) Applicant: Anna Belman, Campbell, CA (US)

(72) Inventor: Yuri Belman, Campbell, CA (US)

( * ) Notice: Subject to any disclaimer, the term of this patent is extended or adjusted under 35 U.S.C. 154(b) by 110 days.

(21) Appl. No.: 16/349,546

(22) PCT Filed: Nov. 14, 2017

(86) PCT No.: PCT/US2017/061538
§ 371 (c)(1),
(2) Date: May 13, 2019

(87) PCT Pub. No.: WO2018/090000
PCT Pub. Date: May 17, 2018

(65) Prior Publication Data
US 2019/0282255 A1    Sep. 19, 2019

Related U.S. Application Data

(60) Provisional application No. 62/421,874, filed on Nov. 14, 2016.

(51) Int. Cl.
*A61B 17/295* (2006.01)
*A61B 17/12* (2006.01)
(Continued)

(52) U.S. Cl.
CPC ...... *A61B 17/295* (2013.01); *A61B 17/12009* (2013.01); *A61B 17/12013* (2013.01); *A61B 17/285* (2013.01); *A61B 2017/00818* (2013.01)

(58) Field of Classification Search
CPC .......... A61B 17/12013; A61B 17/0491; A61B 17/06114; A61B 17/0483; A61B 17/06061; A61B 17/122; A61B 17/12; A61B 17/12009; A61B 17/12018; A61B 2017/0475; A61B 2017/0477;
(Continued)

(56) References Cited

U.S. PATENT DOCUMENTS 3,841,521 A    10/1974 Jarvik
4,569,346 A    2/1986 Poirier
(Continued)

FOREIGN PATENT DOCUMENTS

EP    2108316 A1    10/2009
RU    2080094 C1    5/1997
(Continued)

OTHER PUBLICATIONS

Written Opinion of the International Searching Authority dated Feb. 21, 2018, for corresponding PCT/US2017/061538, 4 pages.
(Continued)

*Primary Examiner* — Kathleen S Holwerda
*Assistant Examiner* — Lauren Dubose
(74) *Attorney, Agent, or Firm* — Cozen O'Connor

(57) ABSTRACT

Cartridges and methods for ligation or dissection and ligation of tubular tissue structures are described. The cartridges and methods provide a means for efficient dissection and application of one or more ligatures by a single user using a single cartridge resulting in effective closure of a vessel or other tubular tissue structure by placement of a ligature at the desired location resulting in the desired tissue margin or stump.

12 Claims, 12 Drawing Sheets

(51) Int. Cl.
*A61B 17/285* (2006.01)
*A61B 17/00* (2006.01)

(58) Field of Classification Search
CPC .. A61B 2017/0479; A61B 2017/12004; A61B 17/295; A61B 17/285
See application file for complete search history.

(56) References Cited

U.S. PATENT DOCUMENTS

| | | | | |
|---|---|---|---|---|
| 5,336,229 | A * | 8/1994 | Noda | A61B 17/12013 606/139 |
| 5,797,958 | A * | 8/1998 | Yoon | A61B 17/122 606/139 |
| 6,610,072 | B1 * | 8/2003 | Christy | A61B 17/0483 606/144 |
| 8,075,573 | B2 * | 12/2011 | Gambale | A61B 17/0469 606/145 |
| 8,715,302 | B2 | 5/2014 | Ibrahim et al. | |
| 10,499,917 | B2 | 12/2019 | Scheib et al. | |
| 2004/0138704 | A1 * | 7/2004 | Gambale | A61B 17/0469 606/213 |

FOREIGN PATENT DOCUMENTS

| | | |
|---|---|---|
| RU | 2257862 C1 | 8/2005 |
| WO | 2011054000 | 5/2011 |

OTHER PUBLICATIONS

Substantive Examination Report of Russian Application No. 2019118412/14 dated Apr. 29, 2020.
Notice of Allowance of Russian Application No. 2019118412/14 dated Feb. 25, 2021.
Echelon Flex Endopath Stapler.

* cited by examiner

US 11,253,282 B2

DISSECTION AND LIGATION CARTRIDGE

CROSS-REFERENCE TO RELATED APPLICATIONS

This application is a 35 U.S.C. § 371 National Stage Application of International Application No. PCT/US2017/061538, filed on Nov. 14, 2017, which claims the benefit of priority to U.S. Provisional Application No. 62/421,874 filed Nov. 14, 2016, which are incorporated herein by reference in their entirety.

BACKGROUND

Modern surgical techniques and emergency medicine often require the dissection and ligation of vessels and other tubular tissue structures. Current techniques for tubular tissue ligation involve clamping of a tubular tissue structure, followed by placement of a clip or staple having a pair of legs connected at their proximal ends that are squeezed around the vessel or tubular tissue structure flattening it. Proper application of such staples and clips requires technical expertise and it is easy to over- or under-tighten them. Over-tightening can lead to tissue damage and necrosis and under-tightening often results in leakage. In some cases, the legs of a clip or staple may not be squeezed together sufficiently or may separate following application resulting in insufficient ligation of a vessel or other tubular tissue structure leading to leakage or blood loss. Frequently, the tissue structure being ligated is inflamed such that the wall thickness is inconsistent, and the tissue is fragile making effective application of staples and clips without damaging the tissue a significant challenge. Adverse events from the use of clips and staples further include perforation by staples and injury from clips and staples that are left in the body. In addition, it is very difficult to apply the clip or staple at the proper angle to the tubular suture and the size of a clip or staple is often not well matched to the size of the tubular structure being ligated.

The gold standard for tubular tissue ligation involves applying a suture or ligature having a knot that is tightened around the vessel or tubular structure. The knots may be placed too far or not far enough from the dissection site resulting in a stump that is too long increasing the risk of infection or too short increasing the risk of leakage.

Knots may be tied manually or by use of a device that applies and tightens the knot, and may involve tying two or more knots for each dissected structure, one knot at a time. This is a slow process that requires significant skill. Some ligature procedures require one person to manipulate the ligature loop while another person manipulates a tissue grasping instrument. In addition, surgery often has space constraints, making it very difficult to effectively ligate a tissue structure when the process requires more than one set of hands.

In most tubular tissue ligation, it is important to maintain a stump or "tissue margin" adjacent the dissection site. Such a tissue margin ensures that even if there is some physical stress induced at the site, the ligated ends of the tissue will not pull through the tightened suture loop. In currently available tissue ligation devices, improper placement of the ligating loop and knot often occurs frequently due to the inability to stabilize the tissue and the loop, resulting in slippage.

In addition, some tubular tissue structures are smaller than others, and hence a device for tissue ligation must be able to accommodate both large and small tubular structures and be able to ligate a tubular tissue structure that has a variable wall thinness over the section to be ligated with the proper amount of tension to make a knot with the right degree of tightness.

Accordingly, there remains a need for an improved device and method for ligation of tubular tissue structures. The present invention addresses this need.

Figure 1:
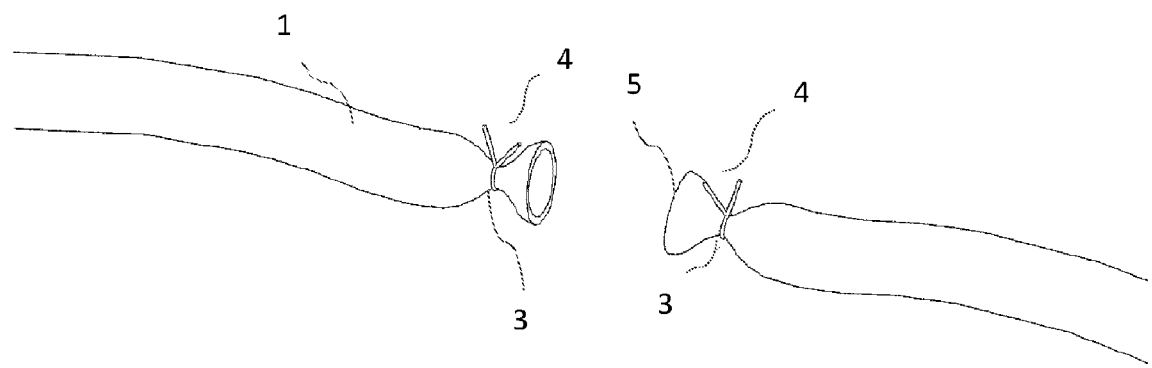
FIG. 1 is a schematic depiction of an exemplary tubular structure that has been dissected with ligature knots applied and tightened at a prescribed distance from each of the dissected ends creating a stump according to certain embodiments of the invention.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It should therefore be understood that any one or more of the teachings, expressions, embodiments, examples, etc. described herein may be combined with any one or more of the other teachings; expressions, embodiments, examples, etc. that are described herein. The following-described teachings; expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein. Other features and advantages of the invention will be apparent from the following detailed description, and from the claims.

Definitions

In describing and claiming the present invention, the following terminology will be used in accordance with the definitions set out below.

The term "comprises", and grammatical equivalents thereof are used herein to mean that, in addition to the features specifically identified, other features are optionally present. For example, a composition or device "comprising" (or "which comprises") components A, B and C can contain only components A, B and C, or can contain not only components A, B and C but also one or more other components. The terms "consisting essentially of" and grammatical equivalents thereof are used herein to mean that, in addition to the features specifically identified, other features may be present which do not materially alter the claimed invention.

The term "at least" followed by a number is used herein to denote the start of a range beginning with that number (which may be a range having an upper limit or no upper limit, depending on the variable being defined). The term "at most" followed by a number is used herein to denote the end of a range ending with that number (which may be a range having 1 or 0 as its lower limit or a range having no lower limit, depending upon the variable being defined). When a range is given as "(a first number) to (a second number)" or "(a first number)-(a second number)", this means a range whose lower limit is the first number and whose upper limit is the second number. The terms "plural", "multiple", "plurality" and "multiplicity" are used herein to denote two or more than two.

Where reference is made herein to "a" or "an" feature, this includes the possibility that there are two or more such features (except where the context excludes that possibility). Where reference is made herein to two or more features, this includes the possibility that the two or more features are replaced by a lesser number or greater number of features providing the same function, except where the context excludes that possibility. The numbers given herein should be construed with the latitude appropriate to their context and expression; for example, each number is subject to variation which depends on the accuracy with which it can be measured by methods conventionally used by those skilled in the art.

The terms "ligature end" or "knot ear" are used herein with reference to the length of ligature that extends beyond a ligature knot. The ligature end or knot ear may be 3 mm or longer, from 2-4 mm, from 2-5 mm, from 3-6 mm, 1 mm, 2 mm, 3 mm, 4 mm or 5 mm for a knot ear that is pre-set on a partially tightened slidable knot. Following tightening of a partially tightened slidable knot 26, the ligature tail 28 may be cut resulting in a knot ear 4 having a length of 3 mm or longer, from 2-4 mm, from 2-5 mm, from 3-6 mm, 1 mm, 2 mm, 3 mm, 4 mm, 5 mm, 6 mm, 7 mm, 8 mm, 9 mm, or 10 mm.

As used herein the term "occlusion", is used with reference to the blockage or closing of a tubular tissue structure.

The term "stump" is used herein with reference to the section of a tubular tissue structure 1 between a tightened ligature knot and the dissected end of the tissue structure.

The terms "stump length" and "length of the stump" are used herein with reference to the distance between the ligature knot and the dissected end of the tubular tissue structure. A stump length may be from about 1 mm to about 15 mm, from about 1 mm to about 12 mm, from about 1 mm to about 10 mm, from about 2 mm to about 8 mm, from about 3 mm to about 7 mm, from about 4 mm to about 6 mm, from about 5 mm to about 7 mm, 3-4 mm, 4-5 mm, 5-6 mm, 6-7 mm, 7-8 mm, 8-9 mm, 9-10 mm, 1 mm, 2 mm, 3 mm, 4 mm, 5 mm, 6 mm, 7 mm, 8 mm, 9 mm, 10 mm, 11 mm, 12 mm, 13 mm, 14 mm, or 15 mm. The stump may be longer on one side than the other.

The terms "tubular structure" and "tubular tissue structure" are used herein with reference to a structure in the body of a human or animal, e.g., a tissue such as an organ or vessel that can be ligated using the cartridges and methods disclosed herein.

This specification incorporates by reference all documents referred to herein and all documents filed concurrently with this specification or filed previously in connection with this application, including but not limited to such documents which are open to public inspection with this specification.

OVERVIEW

The cartridges and methods disclosed herein allow a single person to effectively accomplish ligation of a tubular tissue structure with the desired tissue margin (stump length) in a fraction of the time required for manual ligation. The cartridges and methods can accommodate tubular tissue structures with a wide variation in diameter and wall thickness and do not depend upon the skill of the user. The jaws can accommodate a tubular tissue structure with a diameter of from 2-30 mm.

Use cases for the cartridges and methods disclosed herein include, for example, emergency medicine, human and veterinary surgery including minimally-invasive surgery, general surgery, endoscopy and laparoscopy, and robotic surgery, as further described below.

Products routinely used for ligation in laparoscopic, minimally-invasive and robotic surgical procedures that are staples, clips, and surgical knots, each of which is deficient in one or more ways.

Surgical closure with sutures (loop and knot) is the "gold standard" for surgical ligation. Currently available options include manual tying of a knot (essentially "sewing"), which requires several manual actions. The procedure is slow and requires a high skill level for the surgeon and a trained assistant. A device, the Endoloop® is used for ligation in laparoscopic procedures. It consists of a single long ligature in a plastic tube that is a ligature loop with a knot. The technique of deploying an Endoloop® involves opening the loop, then maneuvering it around the severed tubular tissue structure to be ligated. This involves skill because the Endoloop® is floppy and complex manual actions are required to get it in a good position before it is tightened. The process is slow with multiple instruments and requires a skilled surgeon and an assistant. In addition, such devices apply a single ligature knot, requiring the user to use more than one device in cases where two or more knots are applied during a given procedure.

Surgical closure with U- or V-shaped clips is a relatively fast and easy method to ligate tubular tissue structures and does not require a high level of effort or skill from a surgeon, however, incomplete closure and the possibility of dislodgment and misplacement is inherent to this method. Metal pieces can be left inside the body resulting in injury and interference with CT. MRI and X-ray imaging. In addition, the method can only be used for tubular tissue structures with a diameter of up to 6 or 7 mm.

Surgical closure with stapling techniques offers the advantages of speed (closure in 30 to 60 seconds) as well as simultaneous dissection and ligation (occlusion). Safety problems with use of staples for surgical closure have been acknowledged by the FDA. Adverse events include inadequate closure which can lead to bleeding or internal content leakage due to a discrete line of staples, mismatch of location, tissue ruptures by staple bending, the wrong type of staple closure, and/or a disparity between staples and tissue thickness. If a ligature is under tightened, the tubular structure may leak. If a ligature is overtightened, tissue damage may result. In addition, an excessive number of staples in a cassette may lead to dropping unused ones inside the body. In addition, staples can extend beyond the tissue structure being ligated and cause penetration of neighboring tissue.

Tissue damage may also occur due to staples left in the body which can also interfere with CT, MM and X-ray imaging.

The cartridges disclosed herein address the deficiencies in currently available devices by providing a cartridge that can be employed by a single user with little to no training for safe, fast, consistent dissection and ligation of tubular tissue structures. The cartridge provides for adjustment to the diameter of the tissue structure to be ligated (small or large), has no foreign objects to leave behind in the body, and does not damage surrounding tissue.

In using the cartridge, various embodiments of which are disclosed herein, the compression members or jaws 11 of a grasping or clamping implement 10 functions to limit or stop any movement of the tubular tissue structure 1 after it is grasped or clamped. A ligature loop 6 is pulled such that it slides over the dissected end of the tubular tissue structure and is placed at the desired distance from the dissected end creating a stump 5 of a chosen size. See FIG. 1. The cartridges and methods disclosed herein stabilize both the ligature loop and the tubular tissue and provide for placement of the knot in the desired location. One cartridge may be used to apply one or more ligature knots.

Cartridge Embodiments

Figure 2:
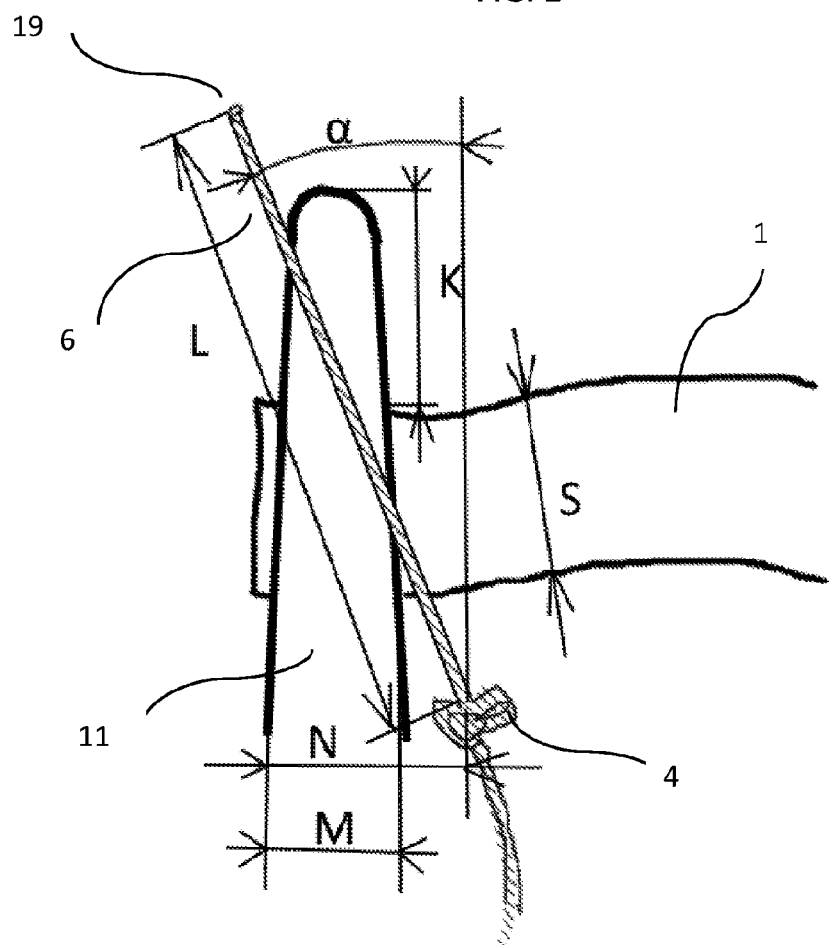
FIG. 2 provides a diagram that shows the relationship of the size of the ligature and the size of the tubular structure to the angle α (of the slanted edge of the cartridge relative to the longitudinal axis of the cartridge) according to certain embodiments of the invention.

As shown in FIG. 2, the relationship between the size of the ligature and the size of the tubular structure to the angle ($\alpha$) of the slanted edge of the cartridge relative to the longitudinal axis of the cartridge. If M is the width of the implement, N is the distance from the distal edge of the implement to the knot position, K is the length of the extended end of the implement, S is the diameter of the tubular structure, and L is the size of the loop, then the following formula applies:

$$\alpha = \operatorname{arctg}((N-M/2)/(S+K))$$

$$L = (S+K)/\cos \alpha$$

In one embodiment, the sleeve 7 of the cartridge 16 can be any shape so long it fits over the surgical instrument 17, e.g., a clamp, used for a given procedure. The sleeve has opposed proximal and distal ends and a wedge-shaped (slanted) distal edge that tapers inwardly. The size and shape of the cartridge sleeve 7 may be varied and correlates with the angle of the slanted edge relative to the longitudinal axis of the sleeve and the desired length of the stump 5.

The slanted edge at the distal end of the cartridge 16 is at an angle of less than 90o and greater than 10o, for example 80-90 o, 75-85 o, 70-80 o, 65-75 o, 60-70 o, 55-65 o, 50-60 o, 45-55 o, 40-50o, 35-45 o, 30-40 o, 25-35 o, 20-30 o, 15-25 o, 10-20 o relative to the longitudinal axis of the tubular structure 1. The size and shape of the sleeve 7 is variable and the sleeve is designed such that the angle of the slanted edge of the sleeve 7 relative to the longitudinal axis of the tubular structure 1 results in placement of the ligature yielding a stump 5 having the desired length. See FIG. 2.

Figure 3:
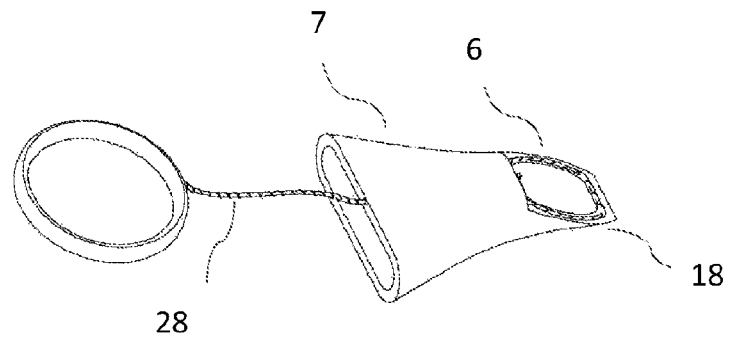
FIG. 3 is a schematic depiction of an exemplary cartridge that has a slanted edge at the distal end, which may be an arch as shown in the figure according to certain embodiments of the invention.
Figure 4:
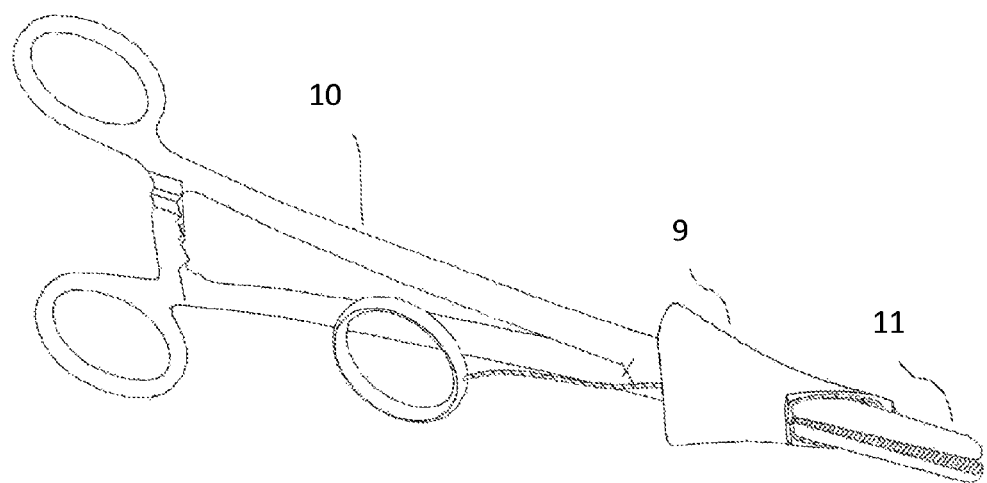
FIG. 4 is a schematic depiction of a single barrel cartridge placed around the mid longitudinal axis of a grasping or clamping instrument which has compression members or jaws at the distal end according to certain embodiments of the invention.

One embodiment of a cartridge for ligating a tubular tissue structure 1 is shown in FIG. 3. In this embodiment, the cartridge has a sleeve 7 that fits over the mid longitudinal axis of a grasping or clamping instrument 10 having jaws 11 that compress the tubular structure as shown in FIG. 4. In this embodiment, the distal end of the sleeve 7 has a slanted edge and a groove 18 for holding at least one ligature. The ligature has a loop 6 at one end secured by a partially tightened slidable knot 26. In this embodiment, the sleeve 7 can be placed around, or be attached to the mid-longitudinal axis or the distal end of any instrument 17 effective to grasp or clamp a tubular tissue structure 1 to be ligated.

Figure 5:
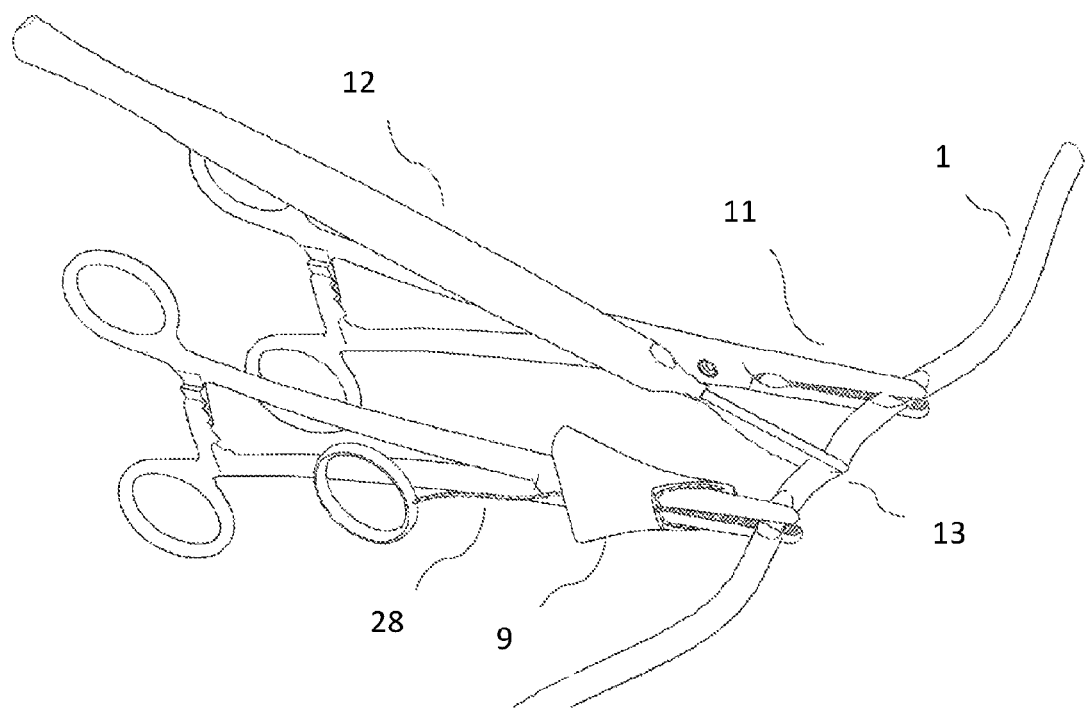
FIG. 5 is a schematic depiction of two independent grasping or clamping instruments, both with distal jaws clamping a tubular structure, and with a single barrel cartridge in a proximal locked position placed around the mid longitudinal axis of the instrument, and an independent cutting implement (scalpel) according to certain embodiments of the invention.
Figure 6:
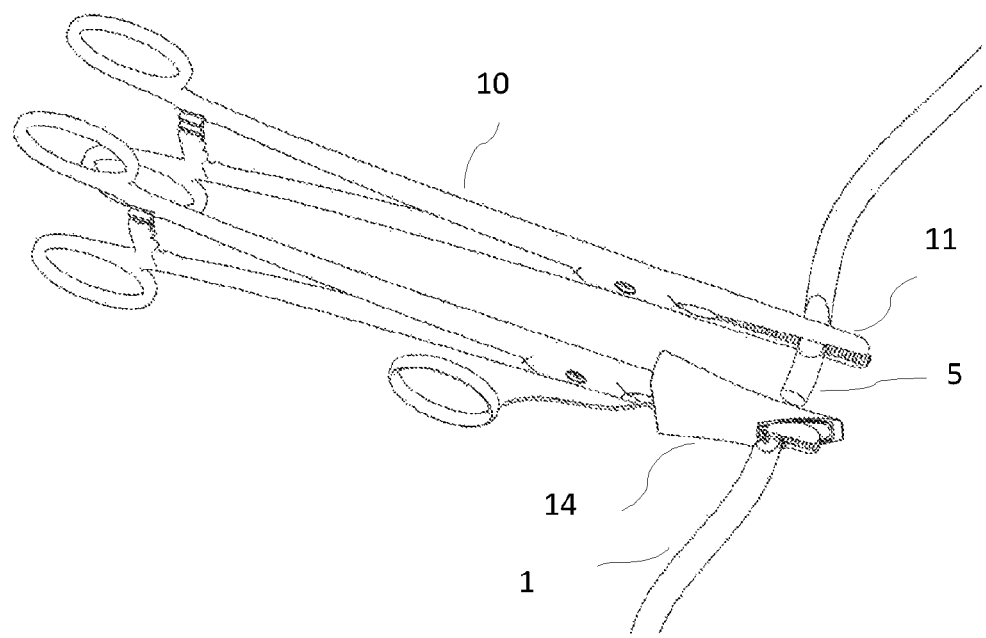
FIG. 6 is a schematic depiction of two independent grasping or clamping instruments, both with distal jaws clamping a tubular structure, and one with a single barrel cartridge in a distal unlocked position according to certain embodiments of the invention.

FIGS. 5 and 6 illustrate one cartridge embodiment wherein two independent grasping or clamping instruments 10 with distal jaws 11 are clamping a tubular structure 1. In FIG. 5, a cartridge has a sleeve 7 that fits over the mid longitudinal axis of one of the grasping or clamping instruments 10 which is in a proximal locked position 9. In this embodiment, the cartridge is used with an independent cutting implement 12 (a scalpel). Some exemplary grasping or clamping instruments 10 for use in this embodiment include clamps, forceps, a hemostat, an endoscopic clamp, a laparoscopic tool, and the like. The cartridge 16 is typically disposable and may comprise grasping or clamping implements 10 or be used with reusable or partially reusable grasping or clamping instruments.

The ligature loop may have a pulling component, for example a ring, attached to the proximal end of the ligature which can slidably move the ligature loop thereby tightening the partially tightened slidable knot 26 around the tubular structure. See FIG. 6, which also illustrates a cartridge in the distal unlocked position 14.

Figure 7:
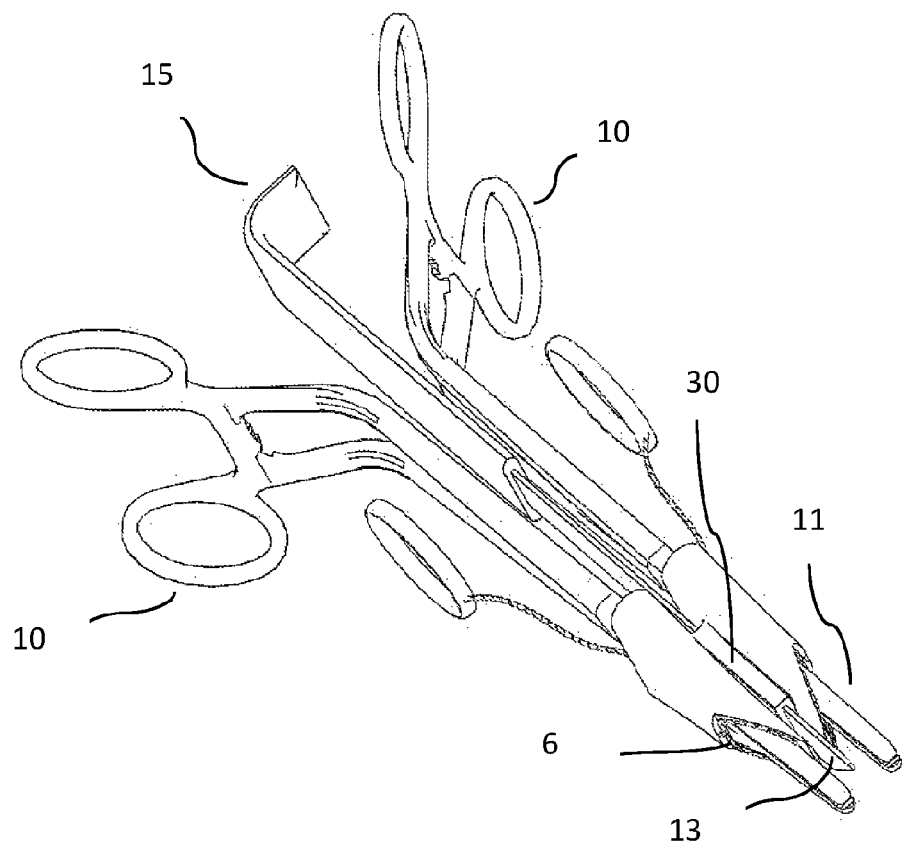
FIG. 7 is a schematic depiction of a double barrel cartridge which includes a slot or guide for moving a cutting implement and a cutting implement that has been engaged and moved to the distal end of the cartridge according to certain embodiments of the invention.

The cartridge may comprise a single barrel or sleeve or two barrels or sleeves. In one embodiment, the cartridge comprises two barrels as shown in FIG. 7. The barrels may have a slanted edge at the distal end 19 and can be placed around or be attached to the mid-longitudinal axis or the distal end of any instrument 10 effective to grasp or clamp a tubular tissue structure 1. In single barrel embodiments, the barrel or sleeve 7 may be on the right or left side to accommodate different users. When the cartridge comprises two barrels or sleeves 7, it may be used with two grasping or clamping instruments 10 that are the same or different. In such cases, a tubular tissue structure 1 may be grasped or clamped on each side of a location to be dissected or cut, after which the tissue is cut and a ligature loop 6 is placed over each side of the dissection site such that a partially slidable knot 26 is tightened at a selected location on each side to yield a stump 5 having the desired length.

Figure 8A:
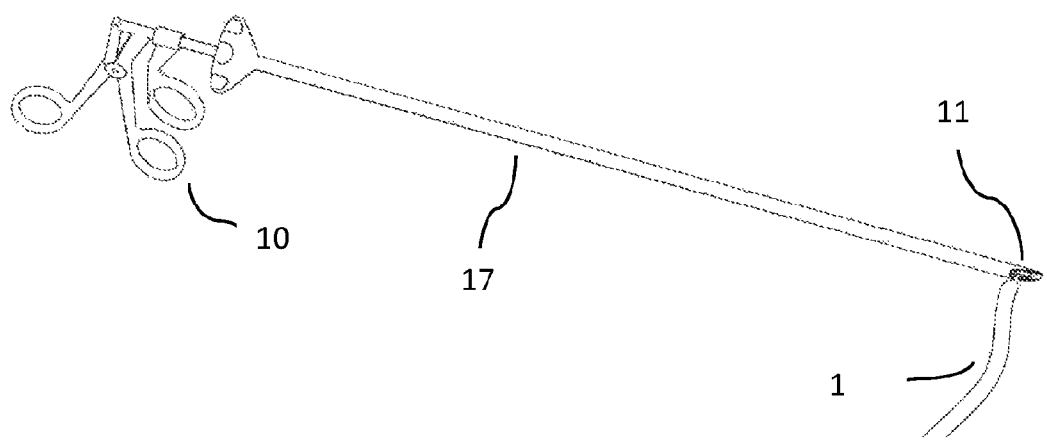
FIG. 8A is a schematic depiction of an elongated cartridge, with a grasping or clamping implement at the distal end that is clamping a tubular tissue structure according to certain embodiments of the invention.
Figure 8B:
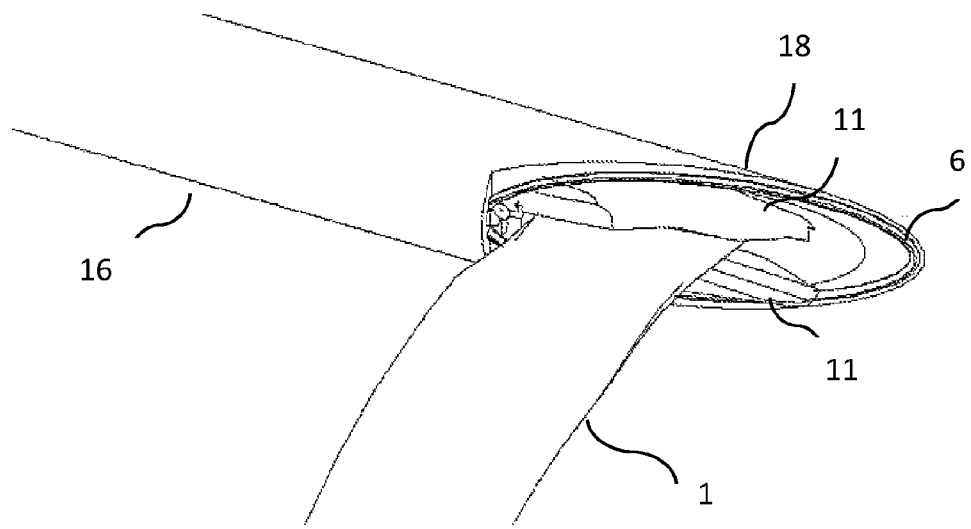
FIG. 8B is a schematic depiction of the distal end of a cartridge showing the jaws of a grasping or clamping implement clamping a tubular structure and the presence of ligature loops in a groove at the distal end of the cartridge according to certain embodiments of the invention.
Figure 8C:
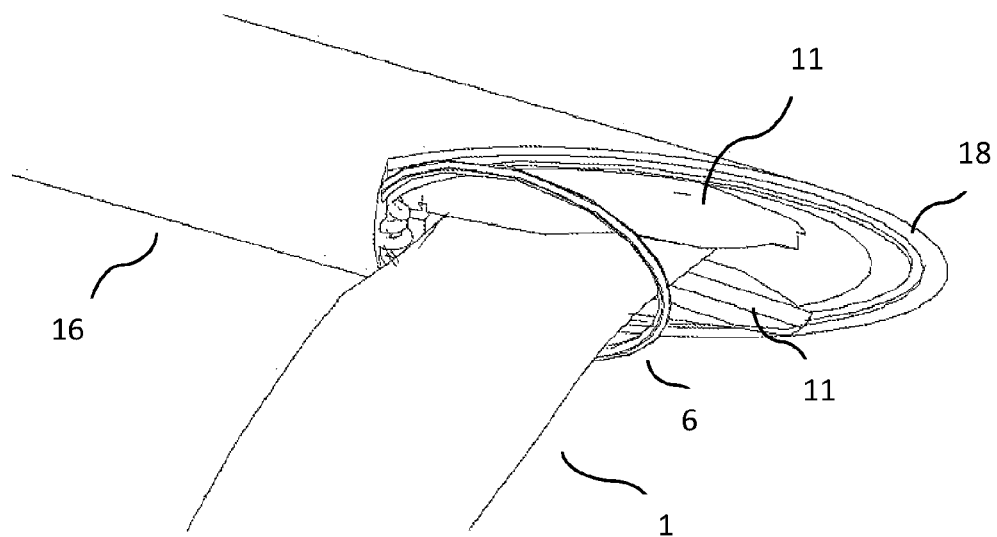
FIG. 8C is a schematic depiction of the distal end of a cartridge showing the jaws of a grasping or clamping implement clamping a tubular structure and a ligature loop which has been moved over the end of the jaws and positioned around the dissected end of a tubular structure according to certain embodiments of the invention.

In some embodiments, the cartridge 16 has a grasping or clamping implement 10 at the distal end with jaws 11 for clamping a tubular structure 1 with ligature loops 6 in a groove 18 at the distal end of the cartridge 16, as shown in FIG. 8B. When the cartridge 16 is actuated, one or more ligature loops 8 are pulled and moved out of the distal groove 18 such that they are in position for a partially slidable knot 26 to be tightened around the dissected end of a tubular tissue structure 1 as shown in FIG. 8C.

Figure 10A:
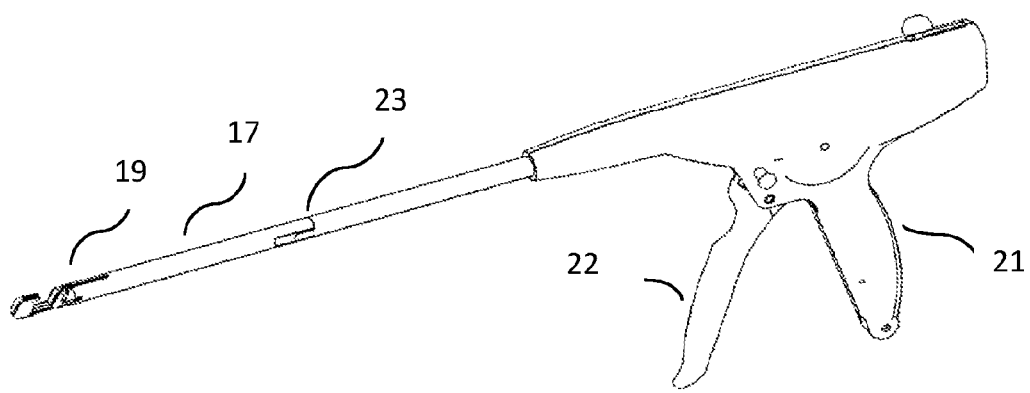
FIG. 10A is a schematic depiction of a device useful for insertion into a trocar for dissection and ligation during laparoscopic surgery. The device has an elongated cartridge with a clamping implement at the distal end attached to a handle which has a handle trigger or actuation engager linked to an actuation mechanism according to certain embodiments of the invention.
Figure 10B:
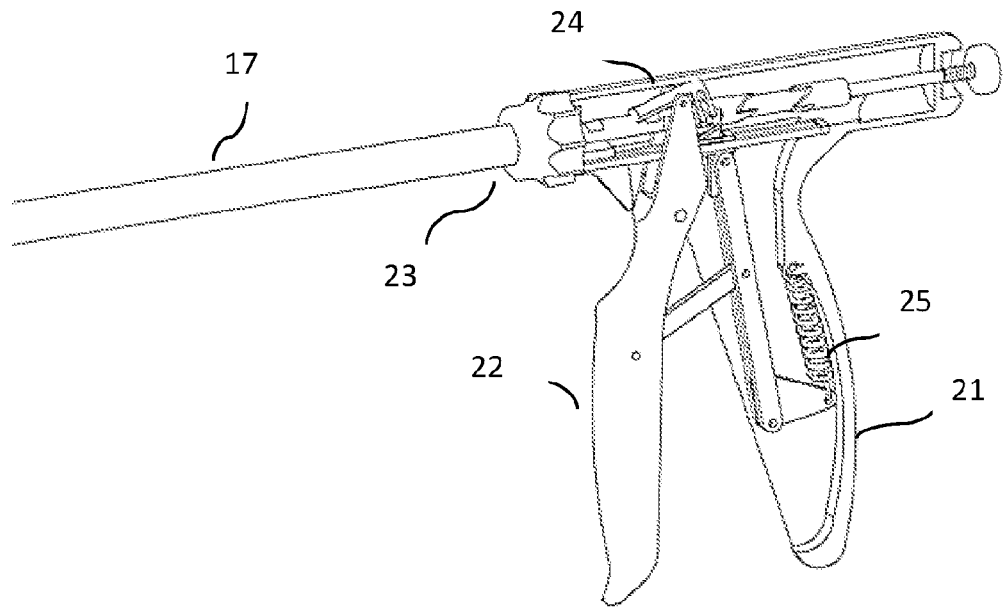
FIG. 10B is a schematic depiction of an exemplary handle attached to an elongated cartridge. The handle has an internal actuation mechanism linked to a spring and a handle trigger or actuation engager according to certain embodiments of the invention.

In some embodiments, the cartridge is elongated as shown in FIG. 8A. The cartridge 16 may be sterile and can be inserted through a trocar 43 for a single use during laparoscopic surgery. An elongated cartridge may be provided in one or more pieces or sections. In some embodiments, such elongated single-use sterile cartridges are attached to a handle 21 prior to use as shown in FIGS. 10A and 10B. The handle may be reusable or disposable and typically comprises an internal actuation mechanism. In some embodiments, the cartridge 16 and/or the handle 21 comprises a trigger or actuation engager 22 linked to an actuation mechanism 24 for moving the cartridge 16 from a proximal locked position 9 to a distal unlocked (engaged) position 14 before a ligature loop 6 can be pulled. In some embodiments, a surgeon or other user can manually extend and retract the cartridge 16. For example, a switch, trigger or button 22 in communication with a locking assembly may be used to cause the locking assembly to release allowing one or more ligatures to be moved.

In some embodiments, a locking assembly, e.g., a cooperating locking assembly maintains the cartridge in a proximal locked position 9 and comprises a release or actuation mechanism 24 which when actuated moves the cartridge to a distal or unlocked position 14. The locking assembly release may be manual or automatic and may comprise a mechanism such that the cartridge can be extended or retracted mechanically and/or electrically. FIG. 10B shows an exemplary handle 21 attached to a cartridge 16 via a simple cartridge/handle interface 23 that has an internal actuation mechanism 24 linked to a spring 25 and a handle trigger or actuation engager 22.

Figure 11A:
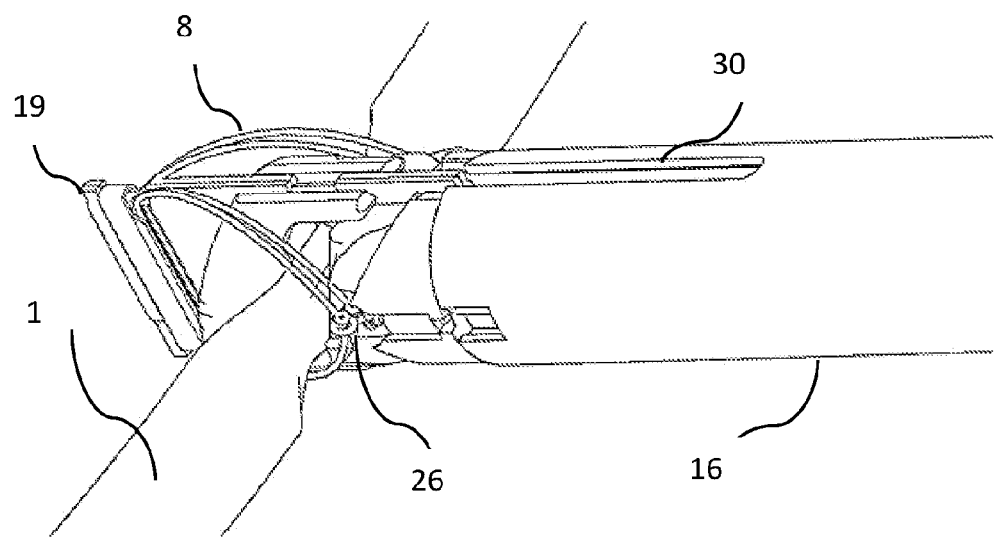
FIG. 11A is a schematic depiction of the distal end of an internal cartridge showing multiple ligature loops pre-positioned in the cartridge and each having a partially slidable knot. The cartridge also has a central slot or guide for a cutting implement according to certain embodiments of the invention.
Figure 11B:
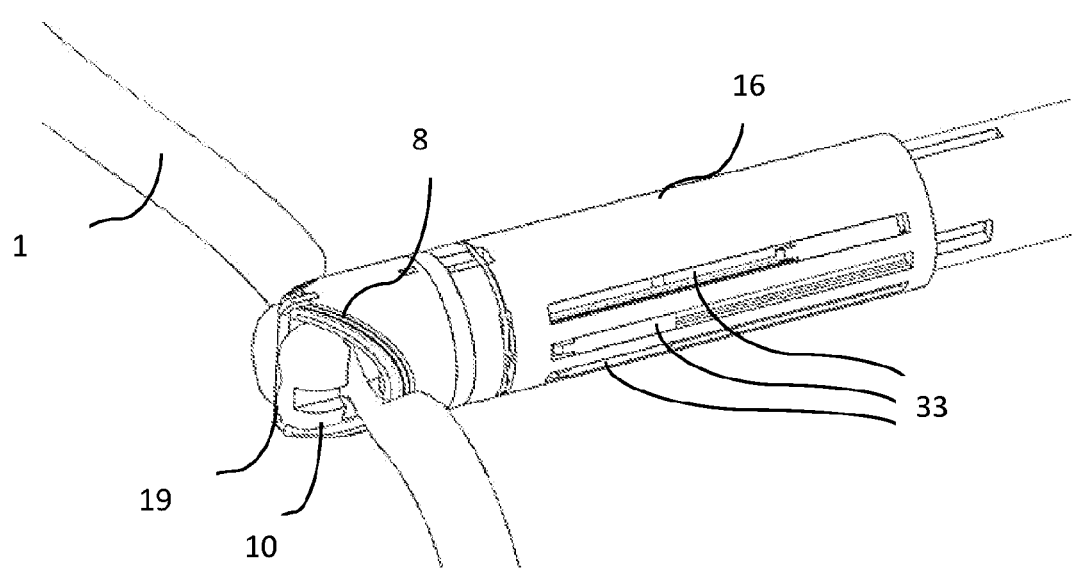
FIG. 11B is a schematic depiction of the distal end of an external cartridge showing the jaws of a grasping or clamping implement clamping a tubular tissue structure with multiple ligature loops pre-positioned in a groove at the distal end of the cartridge according to certain embodiments of the invention.

In some embodiments, the cartridge is an "external" cartridge. As shown in FIG. 11B, the distal end of the external cartridge 41 has a groove 18 (FIG. 11E) that can house one or more ligature loops 8, and a grasping or clamping implement 10 with jaws 11 clamping a tubular tissue structure 1. The figure also illustrates an exemplary tensioner mechanism 33. In some embodiments, the cartridge comprises a mechanism that adjusts the ligature/ligature loop tension by way of a compensator/tensioner mechanism that prevents excessive or insufficient tightening forces in order to achieve appropriate occlusion of each tubular tissue structure. The tensioner mechanism may comprise a spring 32 and may pivot such that different tension is applied to the ligatures on opposites sides of a dissected tubular structure. The tensioner may be adjustable or non-adjustable. If adjustable, the tensioner mechanism may be automatic. One or more ligature loops (1, 2, 3, 4, 5, 6, 7, 8, 9, 10, 11, 12, 13, 14, or more) may be installed in the cartridge, and each loop can be selected and tightened by an individual tensioner mechanism. By way of example, in some embodiments, the cartridge is equipped (pre-loaded) with 2 to 4 or more ligatures. There may be 1, 2 or more ligatures on each side of the cartridge, for example in the following combination (1+1); (1+2 or 2+1), or (2+2). Ligatures made of the same material with the same diameter, may have differences in stretch ability, strength of ligature material and strength of the knot, which can lead to uneven tightening of the ligature loops. In such cases, the tensioner mechanism will compensate for differences in the ligatures, as well as differences in the diameter and compressibility of the tubular tissues structures being ligated.

Figure 11C:
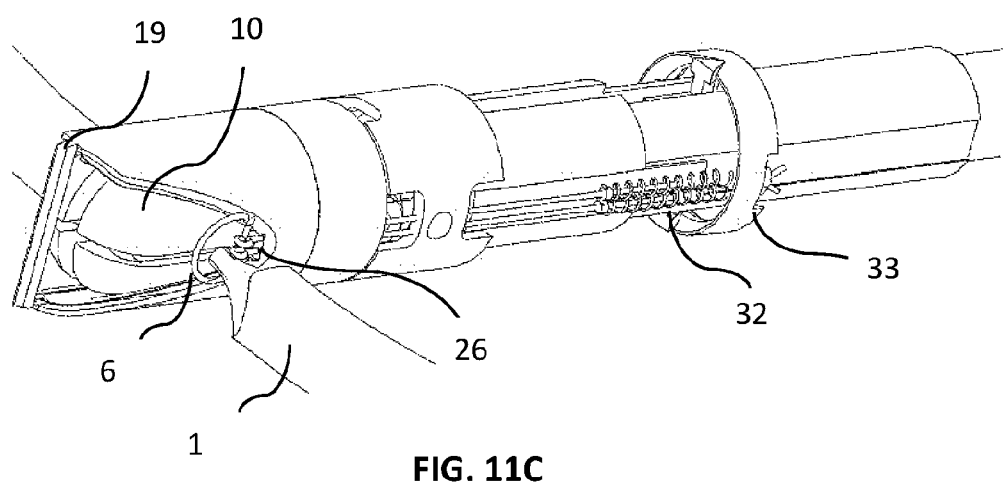
FIG. 11C is a schematic depiction of the distal end of an external cartridge showing the jaws of a grasping or clamping implement clamping a dissected tubular tissue structure with a single ligature loop with a partially slidable knot pre-positioned adjacent the end of the dissected tubular structure. The figure also shows a knot holder and an exemplary tensioner mechanism comprising a spring according to certain embodiments of the invention.
Figure 11D:
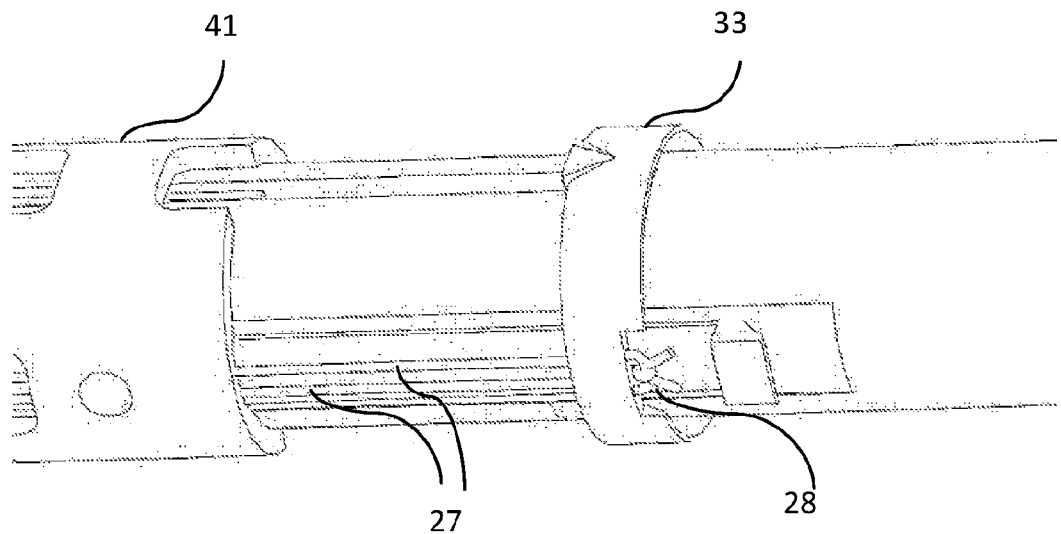
FIG. 11D is a schematic depiction of the distal end of an external cartridge showing the tensioner mechanism; the partially slidable knot of a ligature loop, and a knot holder for holding ligature loops before they are released according to certain embodiments of the invention.
Figure 11E:
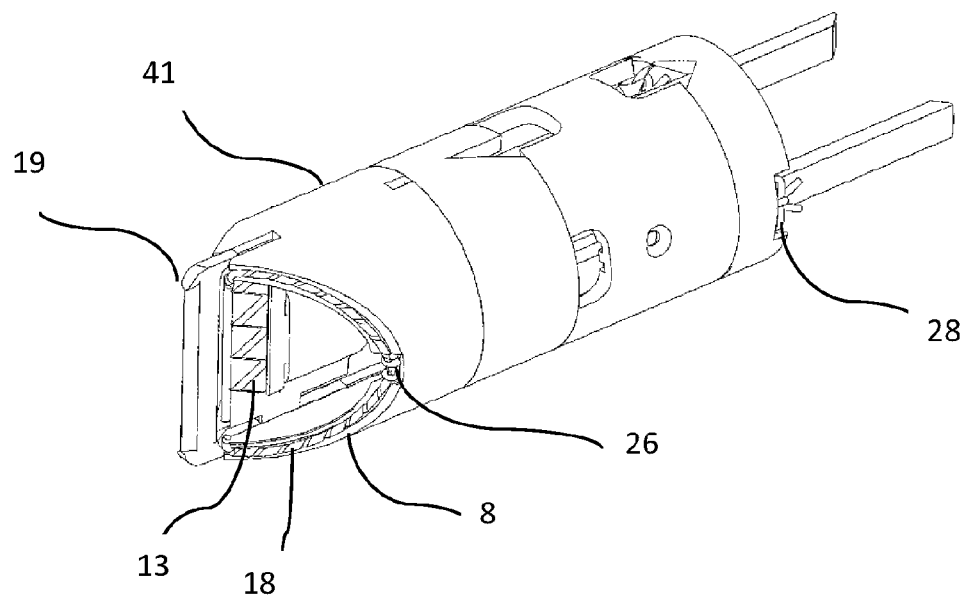
FIG. 11E is a schematic depiction of the distal end of an external cartridge with multiple ligature loops pre-positioned in a groove at the distal end of the cartridge. An exemplary blade having a serrated cutting edge directed distally is positioned to move forward and cut the tubular tissue structure according to certain embodiments of the invention.

In some embodiment, the cartridge or an attached handle comprises an actuating mechanism and the cartridge operates according to the following process: (1) a tubular tissue 1 is compressed with the jaws 11 of a grasping or clamping implement 10, (2) the actuator 24 is triggered; (3) the cartridge tensioner 33 (e.g., a tensioner ring) adjusts the compression force to apply the appropriate amount of tension to each side of the intended dissection point, (4) the knife or blade 13 moves towards the distal end of the cartridge 19 and dissects the tubular tissue structure 1, (5) ligature loop(s) 8 are pulled and released from the knot holder 34 allowing them to move forward over the distal end of the clamping jaws 11, tightening the loops/ligatures 8, and (6) free ends of ligature are cut 29 to yield knot ears 4 and a stump 5 having the desired length. FIG. 11C illustrates the distal end 19 of an external cartridge 41 in an embodiment where following actuation, the jaws 11 of a grasping or clamping implement 10 have clamped a tubular tissue structure 1, and it has been dissected. A single ligature loop 6 with a partially slidable knot 26 has been pulled and released from a knot holder 34, moved forward and is in position for the knot to be tightened around the dissected end of the tubular tissue structure. The knot holder 34 and tensioner ring 33 are shown in more detail in FIG. 11D, and the ligatures loops 8 in a distal cartridge groove 18, an exemplary blade 13 for dissecting a tubular tissue structure, a partially slidable knot of a ligature loop 26, a blade, and a proximal ligature tail 28 are shown in FIG. 11E. The blade 13 may have cutting edges directed proximally or distally.

Figure 12A:
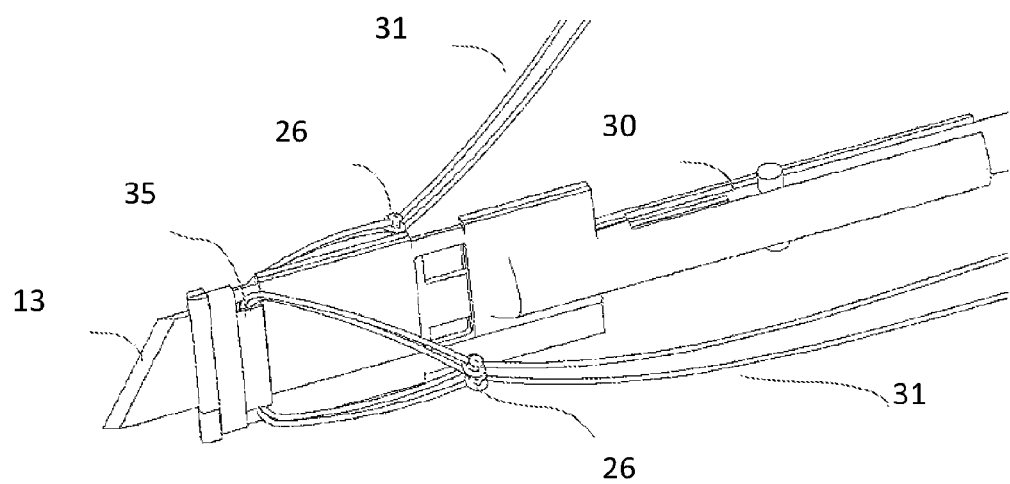
FIG. 12A is a schematic depiction of an internal cartridge showing a wing at the distal end, multiple ligatures each having a partially slidable knot and a proximal ligature tail; and a blade, knife or other cutting implement in a central slot or guide of the cartridge according to certain embodiments of the invention.
Figure 12B:
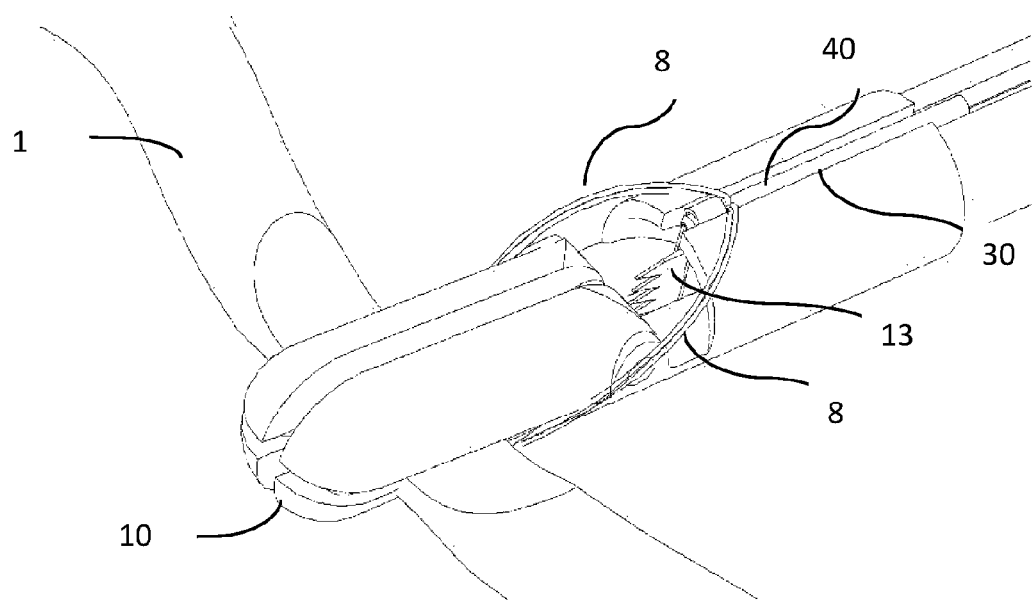
FIG. 12B is a schematic depiction of an internal cartridge housed in a sleeve showing a distal grasping or clamping element with oppositely opposed jaws clamping a tubular tissue structure and the position of a ligature loop on the outside of the cartridge according to certain embodiments of the invention.
Figure 12C:
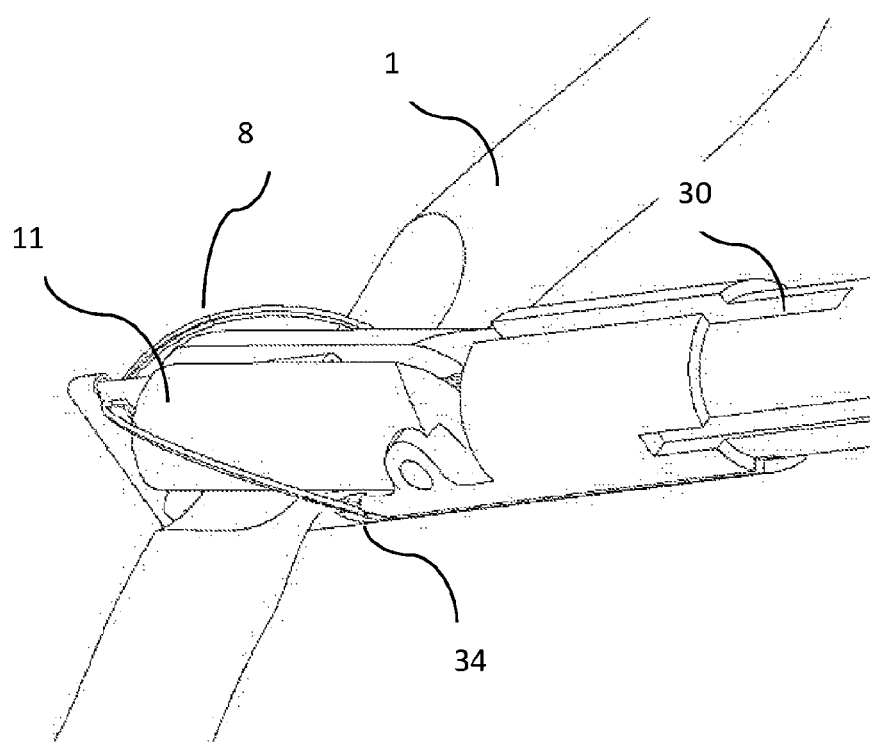
FIG. 12C is a schematic depiction of the distal end of an internal cartridge showing a grasping or clamping element with oppositely opposed jaws clamping a tubular tissue structure and the position of a ligature loop on the top outside of the distal end of the cartridge according to certain embodiments of the invention.
Figure 12D:
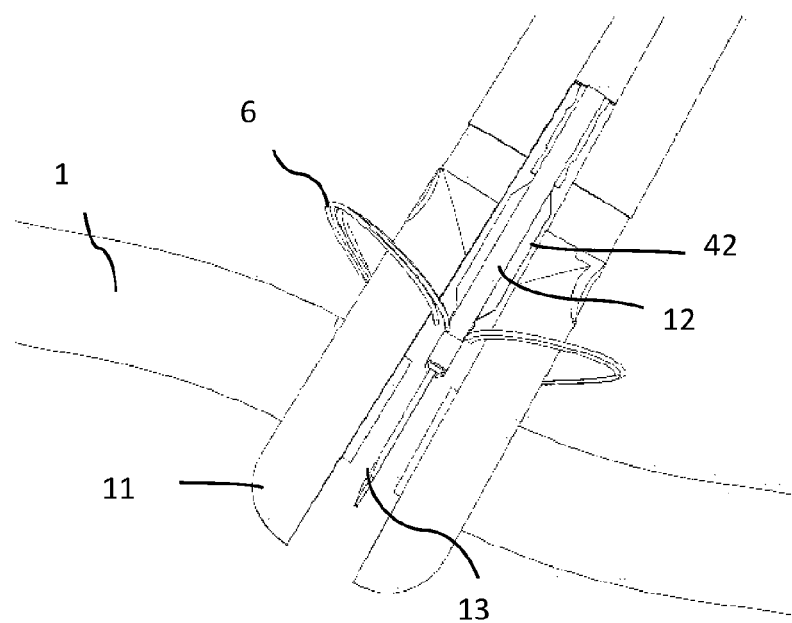
FIG. 12D is a schematic depiction of the distal end of an internal cartridge showing a grasping or clamping element with oppositely opposed jaws clamping a dissected tubular tissue structure, that has been dissected by a blade slidably disposed in a central slot or guide of the cartridge. The figure also shows ligature loops having partially tightened slidable knots positioned on the outside of the internal cartridge with wings released such that they can be pulled over the dissected ends of the tubular tissue structure to tighten the knots according to certain embodiments of the invention.

In some embodiments, the cartridge is an "internal" cartridge. As shown in FIG. 11A, the internal cartridge 40 has one or more ligature loops (each having a partially slidable knot), pre-positioned ("pre-loaded") in the cartridge 16 or 17, and a central slot or guide 30 for a cutting implement such as a blade or knife. As shown in FIG. 12A, the internal cartridge 40 has a wing 35 at the distal end 19 holding one or more ligature loops 8 adjacent the cartridge, each ligature loop having a partially slidable knot 26 and a proximal ligature tail 28. The internal cartridge 40 also has a blade, knife or other cutting implement 13 in a central slot or guide 30 of the cartridge. In some embodiments, an internal cartridge 40 is housed in a sleeve and as shown in FIG. 12B, and the blade 13 may have a serrated cutting edge directed distally such that it is positioned to move forward toward the distal end of the cartridge to cut (dissect) the tubular tissue structure. FIG. 12C illustrates the distal end 19 of an internal cartridge 40 in an embodiment where following actuation, the jaws 11 of a grasping or clamping implement 10 have clamped a tubular tissue structure 1, and it has been dissected. One or more ligature loops 8 have been pulled and released from a knot holder 34, and moved forward to a position such that the knot of each ligature can be tightened. The next step in operation of the internal cartridge is shown in FIG. 12D, where a blade, knife or other cutting implement slidably disposed in a central slot or guide of the cartridge has dissected or cut a tubular tissue structure and one or more ligature loops having partially slidable knots are positioned on the outside of the internal cartridge with wings released such they can be pulled over the dissected ends of the tubular tissue structure and pulled to tighten the knots.

In some embodiments, the cartridge is attached to a handle which may be squeezed (engaged) one time to dissect the tubular structure, and squeezed (engaged) again to release one or more ligature loops from the knot holder and pull the ligature loop over the top of the cartridge, pulling and tightening the ligature loop to generate a knot around the tubular structure that was dissected. In this embodiment, by squeezing the handle, the user engages the cartridge and initiates a sliding action such that ligature loops can move over the distal end of the cartridge and be tightened around the stump or stumps created by the dissection, resulting in a knot or knots in the desired location with the correct amount of tension. In some embodiments, the cartridge comprises 2 plates and wings that hold the ligature loops in place. In some embodiments, the cartridge may provide and tighten ligature loops on one side of the dissection point or provide and tighten ligature loops on both sides of the dissection point. In some embodiments, the internal cartridge comprises a movable flat plate with flexible wings/holders/plates and/or positioning grooves for ligature loops. The blade moves in a central slot or guide inside the cartridge and stops at the distal end of the cartridge, so the blade is never exposed beyond the distal end of the jaws.

Figure 13:
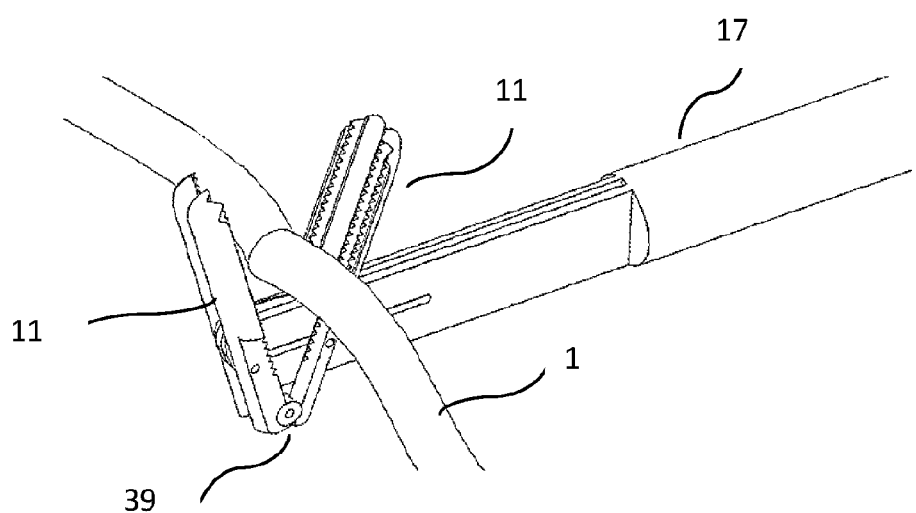
FIG. 13 is a schematic depiction of the distal end of a cartridge showing a grasping or clamping element with oppositely opposed jaws adjacent a tubular tissue structure wherein the grasping or clamping implement has an articulating clamp head, wherein the jaws can be rotated to be at the optimal angle for dissection and ligating of a tubular structure according to certain embodiments of the invention.

In some embodiments, the cartridge has an articulating grasping or clamping head 39 at the distal end of the cartridge 19, such that the jaws 11 can be rotated to be at the optimal angle for dissection and ligation of the subject tubular structure. (See FIG. 13.)

In some embodiments, the cartridge may be disposable, sterile and used a single time. In one embodiment, elongated, single-use sterile cartridges are provided in sterile packaging for use in laparoscopic procedure and the size of the elongated cartridge may be chosen to fit the trocar that is used for a specific laparoscopic procedure, e.g., 12 mm, 10 mm, 8 mm, 7 mm, 5 mm, and the like. Current devices available for ligation during laparoscopic surgery are not disposable and suffer from issues including a lack of sterility and damage to the reusable elongated arm. In addition, currently available laparoscopic devices can ligate, however, they are not capable of also dissecting a tubular tissue structure. Hence, in current laparoscopic procedures, a different device or component must be used for dissection than the device or component used for ligation.

In some embodiments, the cartridge comprises an actuation mechanism for moving the cartridge from a locked position to an engaged position before a ligature loop can be pulled. In some embodiments, a surgeon or other user can manually extend and retract the cartridge. For example, a switch, trigger or button in is communication with a locking assembly such that movement of the switch, trigger or button is effective to cause the locking assembly to release allowing the ligature to be moved. In some embodiments, a locking assembly, e.g., a cooperating locking assembly maintains the cartridge in a proximal locked position 9 and comprises a release or actuation mechanism which when actuated moves the cartridge to a distal or unlocked position 14. The locking assembly release may be manual or automatic and may comprise a mechanism such that the sleeve can be extended or retracted mechanically and/or electrically. FIG. 8C shows a ligature loop that has been pulled and moved out of the distal groove such that it is in position for a partially slidable knot to be tightened around a dissected end of a tubular tissue structure.

A single cartridge may hold one or more ligature loops. The ligature loops may be preloaded into a single groove on top of one another or adjacent one another, or each ligature loop may be in a separate groove. A groove 18 may hold more than one ligature loop 6, e.g., side-by-side or one top of one another. The groove may be on the inside or outside of the cartridge. In embodiments where there is more than one ligature loop, each ligature loop is independently tightenable and the ligature loops are released one at a time from the groove of the cartridge. The groove of a cartridge may hold from 1 to 5, 1 to 10, 1 to 15, 1 to 20, 1 to 25, 1 to 30, 1, 2, 3, 4, 5, 6, 7, 8, 9, 10, 11, 12, 13, 14, 15, 16, 17, 18, 19, 20, 21, 22, 23, 2, 25, 26, 27, 28, 29 or 30 ligature loops, wherein each ligature loop is independently tightenable. One or more ligature loops may be pulled at the same time. Ligature loops may be tightened by pulling them around the side(s) or over the top of the cartridge.

In some embodiments, the jaws of a grasping or clamping implement of a cartridge are used to compress a tubular tissue structure before it is dissected. In some embodiments, the grasping or clamping implement is used to compress a tubular structure that was previously severed or cut, for example in an accident or during a surgical procedure. In either case, the cartridge disclosed herein may be used to place and tighten a ligature knot around the tubular structure.

In some embodiments, the cartridge comprises a knot holder located on the sleeve wherein the knot holder has a locked position and comprises a release which when actuated allows a ligature to be pulled. The knot holder may hold one or more knots, wherein one knot is released each time the knot holder release is actuated.

The cartridge may be made from any medical grade material, for example a material that is or can be FDA approved for use in a medical device. The material may be one or more of pliable, soft, rubbery or rigid and may be made by any method. Exemplary materials include but are not limited to silicone, resin-reinforced silicone, partially crosslinked elastomers (e.g. gels), resins and metal.

Ligatures

Any type of ligature (also referred to as a "suture") can be used in the cartridges and methods disclosed herein, independent of material, stiffness, diameter and other characteristics. The ligature may comprise any suture material including dissolvable (absorbable) or non-dissolvable (non-absorbable) suture material or metal wire. Various sized knotting elements can be used and ligatures with different diameters can be used to complement a particular sized knotting element and/or a particular procedure. The ligature can be flexible to allow it to be manipulated and bent as needed, and can have a stiffness that allows it to retain a certain configuration once moved into that configuration and the stiffness of the ligature can be such that when pushed through the knotting element (or partially slidable knot) to adjust and/or enlarge the size of the loop of the ligature, it does not collapse. The ligature can be biocompatible and/or bioresorbable, and can be formed of any material known in the art for forming a knot to ligate a tubular structure inside the body of a human or animal.

Ligatures may be monofilament or braided and of any size appropriate to the procedure being conducted. The size of ligature material is measured by its width or diameter and is vital to proper tubular tissue ligation. Monofilament ligatures are usually non-absorbable. Braided ligature usually may cause a greater inflammatory response; however, they require fewer ties to maintain the knot integrity. These include silk, cotton and polyester fibers. Ligatures may be absorbable or non-absorbable. Absorbable ligatures are made of materials which are broken down in tissue after a given period of time. Absorbable ligatures may be natural, e.g., catgut, or synthetic, e.g., polymer fibers, which may be braided or monofilament. Natural absorbable ligatures may be plain catgut or chromic catgut and synthetic absorbable ligatures include, but are not limited to polyglycolic acid ligatures, polyglactin ligatures (pgla ligatures), poliglecaprone ligatures (monocryl) (pgcl ligatures), and polydioxanone ligatures (pds). Non-absorbable ligatures include but are not limited to natural fiber, silk, and artificial fibers, such as polypropylene, polyester or nylon, and stainless steel wire.

Ligature Knots

An adequate closure of a dissected end of a tubular tissue structure is vital to minimize surgical site bleeding and infection. A knot should secure the tissue and be simple, easy, quick and reliable. A good knot must be properly formed so the ligature does not slip or cut into itself, and must be easily tightened to ensure maximum strength. The knot must resist slippage when a load is applied to it and must maintain a tight ligature loop as a knot is tied.

Compound sliding knots have more than one turn of the wrapping strand, for example, any sliding knot other than a half hitch. It is preferred that a knot is partially tightened with a ligature loop that slides smoothly and freely without unraveling, jamming prematurely or cutting through tissue as it slides.

Many sliding knots may be used in the cartridges and methods described herein, including but not limited to a Duncan loop, Nicky's knot or taut-line hitch, a surgeon's knot, a Tennessee slider, Roeder's knot, an SMC knot, a Weston knot, Meltzer's knot, Tayside knot, two half-hitches, reversed half-hitches, a practical knot (simple or advanced version), a giant knot, a modified taut line hitch, a clinch knot, a secure knot, Mishra's knot, a blood slipknot, a Hangman's knot, a Hangman's tie, and a combination or variant thereof. See, e.g., Akindele et al., 2014, WJOLS, 7(1) 28-32.

Ligature loops and sliding knots for use in the cartridges and methods disclosed herein must be capable of being handled in a stable manner to encircle and close around a tubular structure in a precise and accurate manner resulting in effective ligation and the desired stump length. One or more knots may be applied to a tubular structure using a single cartridge and methods disclosed herein. Ligatures comprise a sliding loop and can be single, double or triple. A ligature is pulled to place the knot around the tubular structure to be ligated. In some embodiments, the pulling force used to tighten the knot is adjustable using software. In other cases, the pulling force used to tighten the knot is applied manually.

Dissection and Cutting Implements

In some embodiments, the device is used only for ligation, e.g., in the case of trauma, where the device provides a means to quickly ligate a tubular structure (i.e., a blood vessel) that has been severed.

In general, the cartridge comprises a blade or knife and is used for dissection and ligation. In such embodiments, the cartridge includes a blade or knife, for example, a single use, disposable blade or knife. This provides advantage over currently available options, such as sterility and time savings.

In some embodiments, the cartridge comprises a guide for a cutting implement such as a blade or knife that slides within the guide into the cutting position, but cannot extend beyond the distal end of the cartridge. The knife or blade is actuated when it is engaged. Such actuation may be manual or automatic. Blades, knives and other cutting implements for use in the cartridge may have any shape and cutting edge that is effective to dissect the tubular tissue structure of interest. Examples include, but are not limited to, spear-shaped, curved or rounded, dovetail-shaped, flat, concave, convex, double-edged, single edged, having teeth, and serrated blades, knives and other cutting implements.

Methods

The cartridges described herein may be used in any surgical procedure. For example, the cartridge may be used in minimally invasive surgery, open surgery, laparoscopic, robotic, or endoscopic procedures.

In some embodiments, the methods may be used to ligate any animal or human tubular tissue structure by carrying out the steps of constricting and thus stabilizing the tubular tissue structure with the jaws of a grasping or clamping implement prior to ligation, slidably engaging a blade or knife moving it through a central guide or channel to the distal end of the cartridge such that the blade or knife dissects or cuts the tubular tissue structure resulting in dissected ends, pulling the proximal end of one or more ligature loops, releasing them from the cartridge such that when the ligatures move over or around the distal end of the cartridge and over the dissected end of the tubular tissue structure, they can tighten a partially tightened slidable knot around the dissected ends of a tubular tissue structure resulting in a knot and generating a stump of the desired length. After the ligature is pulled and the knot is tightened, the method may further comprise cutting the proximal tail of the ligature generate a ligature end or knot ear using any cutting implement effective under the circumstances. All the steps of the method may be carried by a single user.

Utility

The cartridges and methods disclosed herein can be used to ligate any tubular tissue structure within the human or animal body. Some examples include blood vessels, lymph vessels, portions of the digestive tract, fallopian tubes, colorectal and other polyps, cancerous and other diseased tissue, portions of the digestive tract, the appendix, the gall bladder, the trachea, and the spleen.

More specifically, exemplary procedures wherein the cartridge of the invention may be employed are general surgery, including but not limited to, appendectomy (closure of appendix and mesentery), cholecystectomy (closure of cystic artery and duct), splenectomy (closure of splenic vessels), pancreatic duodenal resection (closure of common bile duct and artery); urology, e.g., nephrectomy (ligation of ureter and renal vessels); varicocoelectomy (closure of testicular veins); gynecology, e.g., tubectomy and adnexectomy and female sterilization (closure of fallopian tubes), and robotic surgery.

Robotic systems may be used to aid in surgical procedures. In some embodiments, the cartridges described herein are attached to surgical robots by way of a simple attachment.

Figure 9:
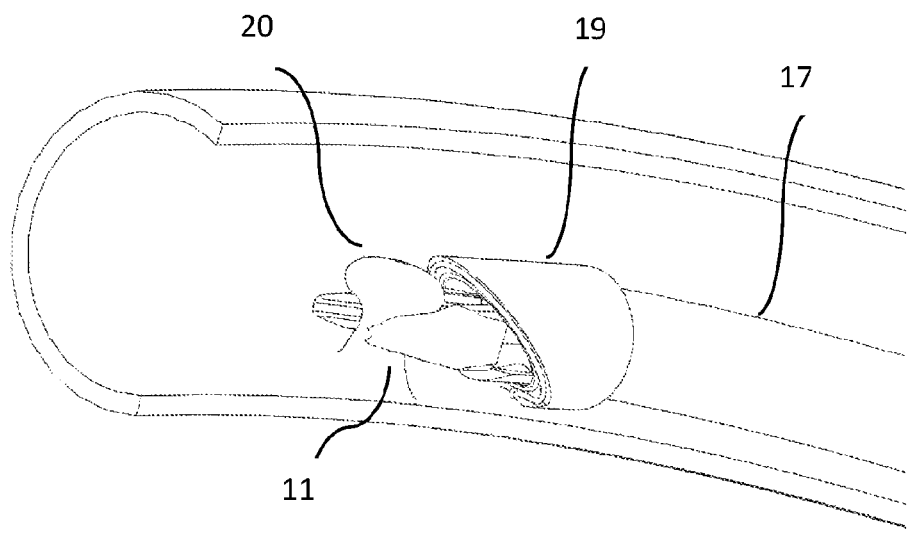
FIG. 9 is a schematic of the jaws of an elongated cartridge grasping or clamping a polyp within a tubular structure according to certain embodiments of the invention.

Endoscopic surgery makes use of a natural orifice and is often used in removal of polyps and other cancerous or diseased tissue. In one embodiment, the cartridge and methods are used for endoscopic surgery, for example in the dissection and ligation of polyps or cancerous or diseased tissue in any of a number of locations. An exemplary elongated cartridge for use in removal of polyps is shown in FIG. 9.

In one exemplary aspect of this embodiment, the cartridge is used in a method for removal of polyps in the digestive tract. In this embodiment, an appropriately sized cartridge may be provided on or attached to an elongated flexible conduit, e.g., a flexible endoscope, that extends from outside the subject through a natural orifice into and along at least a portion of the digestive tract to a target location in the digestive tract. The distal end of the elongated flexible conduit may attach to a cartridge, e.g., an elongated cartridge comprising a grasping or clamping implement.

Current methods for removal of a polyp involve placement of a ligature loop over a polyp which is a difficult procedure when carried out inside a tubular structure in the body. Many current methods for poly removal do not include the step of ligation prior to cutting the polyp resulting in excessive bleeding that is often stopped by ablation which damages adjacent tissue uses well as the tissue that has been cut.

Kits

In some embodiments, a kit is provided that includes a single use sterile cartridge. The kit may also comprise one or more of: (a) ligatures which may be pre-loaded in the cartridge or provided separately; (b) one or more disposable blades or knives; (c) an attachment to increase the length of the cartridge; and (d) a single use or disposable handle. The ligatures may each have partially tightened slidable knots.

Each of components (a)-(d) may also be provided indusial in sterile packaging. In some embodiments, a reusable handle is included in the kit.

What is claimed is:

1. A cartridge for use with a device for dissecting and ligating a tubular tissue structure, the cartridge comprising:
   a generally cylindrical cartridge body having a radial periphery, and a proximal end and an opposite distal end, the proximal end and the distal end defining a cartridge axis;
   a cartridge-base interface at the proximal end, the cartridge-base interface arranged to removably couple the cartridge to a base that includes an actuator operative to move the cartridge from a non-deployed configuration to a deployed configuration;
   a deployable grasping or clamping implement housed within the generally cylindrical cartridge body when the cartridge is in the non-deployed configuration, the deployable grasping or clamping implement having oppositely disposed jaws situated proximate the distal end;
   a deployable cutter assembly housed within the generally cylindrical cartridge body when the cartridge is in the non-deployed configuration, the deployable cutter assembly including a blade movable relative to the generally cylindrical cartridge body along a guide or channel that is arranged along the cartridge axis;
   a first ligature loop holder fixed to the generally cylindrical cartridge body and arranged to retain a first section of a ligature loop to extend along a portion of the radial periphery; and
   a second ligature loop holder fixed to the cutter assembly and arranged to retain a second section of the ligature loop to pass through an interior of the generally cylindrical cartridge body and to be movable relative to the first section along the cartridge axis;
   wherein the deployable grasping or clamping implement is actuatable to grasp or clamp the tubular tissue structure, and the deployable cutter assembly is actuatable to move the blade relative to the generally cylindrical cartridge body to dissect the tubular tissue structure to thereby form a pair of cut ends, and to extend the ligature loop between the cut ends.

2. The cartridge of claim 1, wherein the ligature loop further includes a proximal tail and a partially tightened slidable knot, and wherein the cartridge further comprises:
   a tensioner operative to tighten the ligature loop by pulling the proximal tail through the partially tightened slidable knot.

3. The cartridge of claim 1, wherein the non-deployed configuration comprises a proximal locked position wherein the ligature loop is non-tightenable, and the deployed configuration comprises an unlocked position wherein the ligature loop is tightenable.

4. The cartridge of claim 1, wherein the deployable grasping or clamping implement and the deployable cutter assembly are each actuatable via the cartridge-base interface.

5. The cartridge of claim 1, wherein the first ligature loop holder includes a groove recessed in an exterior surface of the generally cylindrical cartridge body and elongated along a circumferential direction.

6. The cartridge of claim 1, further comprising:
   a third ligature loop holder fixed to the generally cylindrical cartridge body and arranged to retain a third section of a second ligature loop to extend along a portion of the radial periphery; and
   wherein the second ligature loop holder is further arranged to retain a fourth section of the second ligature loop to pass through an interior of the generally cylindrical cartridge body and to be movable relative to the third section along the cartridge axis.

7. The cartridge of claim 1, wherein the first and the second loop holders are each arranged to hold a plurality of sections of a corresponding plurality of ligature loops.

8. The cartridge of claim 1, further comprising:
   a knot holder operative to prevent the ligature loop having a partially tightened slidable knot from being pulled when the cartridge is in the non-deployed configuration.

9. The cartridge of claim 1, further comprising a plurality of ligature loops installed in the first ligature loop holder and the second ligature loop holder.

10. The cartridge of claim 9, wherein each ligature loop of the plurality of ligature loops is independently tightenable.

11. A device for dissecting and ligating a tubular tissue structure comprising the cartridge according to claim 1, and further comprising the base.

12. The device of claim 11, wherein the base comprises a handle and a trigger.

* * * * *